United States Patent [19]

Terneuil et al.

[11] Patent Number: 5,431,822
[45] Date of Patent: Jul. 11, 1995

[54] PROCESS FOR THE CHROMATOGRAPHIC SEPARATION OF A MIXTURE OF POLYGLYCEROLS

[75] Inventors: Gabriel Terneuil, Grenoble; Gérard Hotier, Rueil Malmaison; Daniel Lonchamp, Tassin La Demi Lune, all of France

[73] Assignee: Institut Francais du Petrole, Rueil Malmaison, France

[21] Appl. No.: 197,436

[22] Filed: Feb. 15, 1994

[30] Foreign Application Priority Data

Feb. 15, 1993 [FR] France .................................. 93 01755

[51] Int. Cl.$^6$ .............................................. B01D 15/08
[52] U.S. Cl. ..................... 210/635; 210/656; 210/659; 568/619; 568/621; 568/680; 568/699
[58] Field of Search ...................... 210/635, 656, 198.2, 210/659; 568/619, 620, 621, 679, 680, 699

[56] References Cited

U.S. PATENT DOCUMENTS

| | | | |
|---|---|---|---|
| 3,742,069 | 6/1973 | Hunter | 568/679 |
| 3,968,169 | 7/1976 | Seiden | 568/679 |
| 4,402,832 | 9/1983 | Gerhold | 210/659 |
| 4,614,548 | 9/1986 | Cameron | 210/659 |
| 4,973,763 | 11/1990 | Jakobson | 568/619 |
| 5,122,275 | 6/1992 | Rasche | 210/659 |
| 5,243,086 | 9/1993 | Jakobson | 568/619 |

OTHER PUBLICATIONS

Snyder, Introduction to Modern Liquid Chromatography, Joh Wiley & Sons, 1979, pp. 410–419, 429–438, 519–520, & 621–622.
Revue De L'Institut Francais Du Petrol, vol. 46, No. 6, 1991, Paris, Fr pp. 803–820, G. Hotier et al. "Chromatographie a contre-courant simulé: Développements et perspectives".
Journal Of The Americal Oil Chemists' Society, vol. 44, No. 7, 1967, Champaign US, pp. 376–378, M. R. Sahasrabudeh "Chromatographic analysis of polyglycerols and their fatty acid esters".
Fette, Seifen, Anstrichmittel, vol. 81, No. 11, 1979, Hamburg, DE pp. 436–441, E. Arzberger et al "Analysis of polyglycerols and other polyols from emujlsifiers by HPLC".
Fette, Seifen, Anstrichmittel, vol. 82, No. 3, 1980, Hamburg, DE pp. 93–100, R. Neissner et al "Polyglycerine und fettsäure-polyglycerinpartialester".

*Primary Examiner*—Ernest G. Therkorn
*Attorney, Agent, or Firm*—Millen, White, Zelano, & Branigan

[57] ABSTRACT

A description is given of a process for the separation of at least one constituent from a mixture containing at least two polyglycerols having consecutive degrees of polymerization from 2 to 10, in which said mixture is passed into at least one column lined with an adsorbent particular phase through which flows a liquid eluent, said phase consisting of a cationic organic resin such as a styrene-divinyl benzene copolymer or an anionic resin, or a mineral phase chosen from among silicas, aluminas and zeolites in normal form or modified by grafting, said liquid eluent consisting of an aqueous phase to which is optionally added a strong acid. The process described can be performed continuously or batchwise and in simulated counter-current (SCC) or simulated cocurrent manner.

8 Claims, 3 Drawing Sheets

PROCESS FOR THE CHROMATOGRAPHIC SEPARATION OF A MIXTURE OF POLYGLYCEROLS

The present invention relates to a process for the chromatographic separation of a mixture of polyglycerols.

BACKGROUND OF THE INVENTION

Polyglycerols and their esters have numerous applications. Although at present limited to the foods and cosmetics fields, they are to be extended to petroleum and parapetroleum uses. Thus, the lower derivatives of polyglycerol esters are biodegradable and easily accessible.

It is easy to chemically produce polyglycerols by the action of sodium hydroxide, e.g. on glycerol. This leads to a mixture of polymers with a degree of polymerization (DP) between 2 and 10.

The problem which arises is that of separating the various members of a mixture of polyglycerols, which requires clearly defined cuts. However, as yet there is no satisfactory way for separating the members or groups of consecutive members in a mixture of polyglycerols.

SUMMARY OF THE INVENTION

An object of the invention is to describe a novel process making it possible to solve this problem by chromatographically separating the polyglycerols as a function of their degree of polymerization and with a view to industrial development.

In order to fractionate complex mixtures of polymers, use can be made of combinations of conventional methods and preparative liquid chromatography. Although justified in certain cases, the latter suffer from the disadvantage of being batchwise and requiring excessive solvent and stationary phase quantities.

It is certainly more advantageous to use continuous procedures, particularly in real or simulated countercurrent, or real or simulated cocurrent. It has now been discovered that a suitable association of a particular phase and an eluent, which will be defined hereinafter, makes it possible to obtain particularly satisfactory results with regards to the separation of the different constituents of a mixture of polyglycerols, the process being performable batchwise, but also having the advantage of being performable continuously.

DESCRIPTION OF THE PREFERRED EMBODIMENTS

Figure 1:
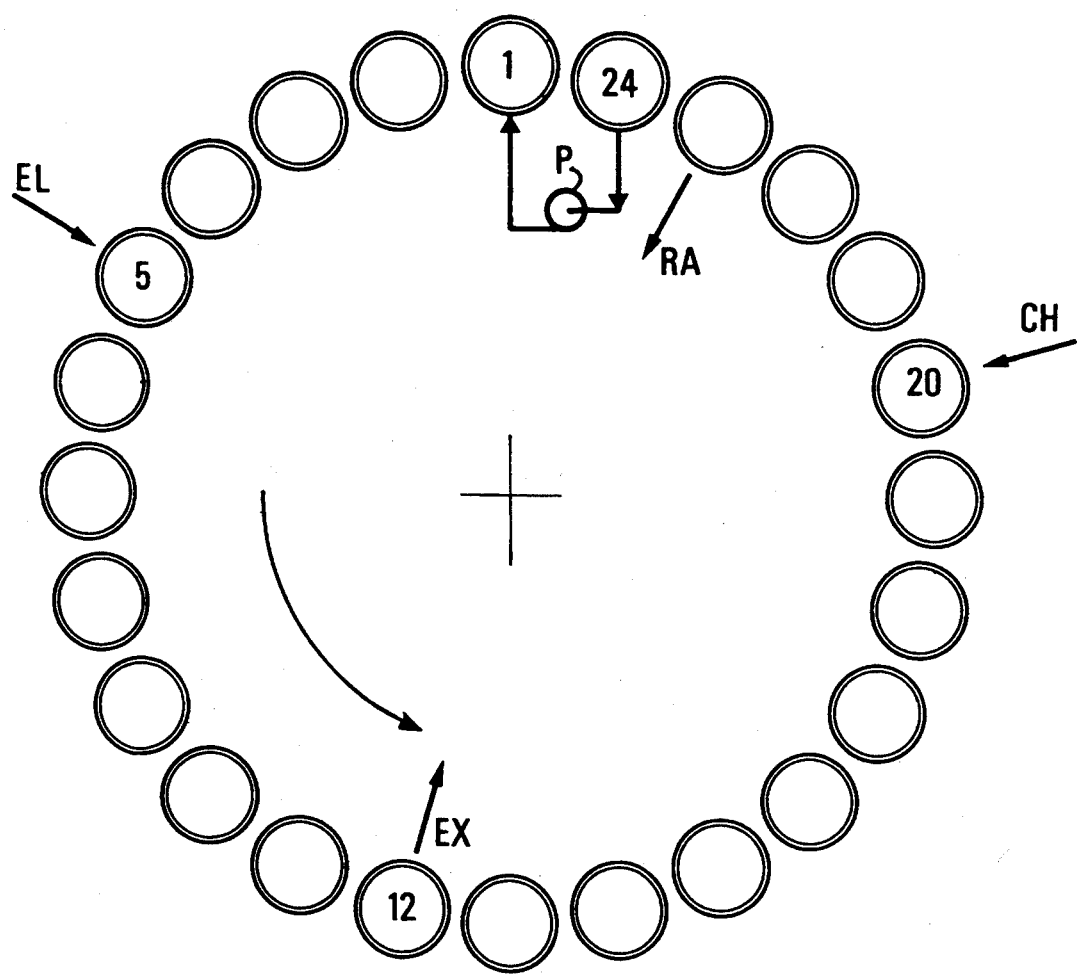
FIG. 1 shows a sequential and synchronous translation of the injection points of the charge (CH) and the eluent (EL), as well as the drawing off points of the extract (EX) and the refined product (RA).

The process for the separation of mixtures of polyglycerols according to the invention can be defined, in general terms, by the fact that a mixture containing glycerol and at least two polyglycerols with consecutive degrees of polymerization DP of 2 to 10, is passed into at least one column in contact with a particular phase able to selectively slow down the migration of the different constituents of the mixture of polyglycerols, an eluent flowing in the said column for entraining the constituents of the mixture at different speeds, said process being characterized in that said particular phase consists of a cationic organic resin such as a cationic divinyl benzene styrene copolymer or an anionic resin or a mineral phase chosen from among silicas, aluminas, silica-aluminas and zeolites in normal form or modified by grafting and in that said eluent consists of a substantially aqueous liquid phase optionally containing a strong acid.

The materials used as the particular phase (or support) in the process according to the invention more preferably contain mineral materials, such as normal silicas, grafting-modified silicas, aluminas or zeolites, or organic materials such as cationic resins (whose cations can in particular be $Fe^{++}$, $Sr^{++}$, $Mg^{++}$, $Al^{+++}$, $Ca^{++}$ or $H^+$) or anionic resins, whose anion can e.g. be $HSO_3$ or the like, or grafted resins of the anionic or cationic type.

The use of organic resins is preferred in the process according to the invention due to their good performance characteristics, bearing in mind their particularly low cost permitting the use thereof on an industrial scale. Use is generally made of resins consisting of divinyl benzene (DVB)-styrene copolymers, whereof the DVB level can be approximately 1.5 to 8.5 wt. %. Their apparent porosity is approximately 50 to 60%.

With regards to their grain size, in general use is made of resins whose particles (which are usually spherical) have very small dimensions, e.g. below 500 micrometers. They can be conventional resins having a relatively broad size distribution around the mean value, or are preferably monocalibrated, spherical resins, e.g. having diameters below 250 micrometers and with a very narrow size distribution. In preferred manner, the cationic resins are used in their acid form ($H^+$) and the anionic resins in their hydrogen sulphite form ($HSO_3^-$), said forms making it possible to obtain better performance characteristics.

The eluent used in the process according to the invention generally consists of an aqueous liquid phase optionally containing a strong acid. In the case where the resin is used in the $H^+$ form, it is particularly interesting to use as the eluent water containing sulphuric acid having a normality of 0.001 to 0.01N.

In the case where a mineral particular phase is used, e.g. a silica, an alumina or a normal or grafted zeolite, the eluent can more particularly consist of pure water.

In general terms, the process according to the invention can be performed at a relatively low temperature, e.g. ranging from ambient temperature to approximately 80° C., using concentrated polyglycerol mixture charges.

The process according to the invention as described hereinbefore can be performed batchwise but also and this is one of its most important advantages, continuously in different ways, namely real or simulated countercurrent, or real or simulated cocurrent.

The process for the separation of mixtures of polyglycerols according to the invention can be used for separating a mixture of polyglycerols into two fractions, one containing polyglycerols with higher DP values than a given value, while the other fraction contains polyglycerols with a DP value of at the most said value, as well as the glycerol. Such a separation takes place by a single passage on the column or columns and then the constituents least adsorbed on the particular phase are eluted first (e.g. the lightest constituents ranging from glycerol to polyglycerol with the chosen DP) and the most highly adsorbed constituents are then eluted (e.g. the constituents whose DP has a value above the fixed value). The elution order is dependent on the chosen eluent-fixed phase pair and it is not impossible to use a reverse order.

The process for separating mixtures of polyglycerols according to the invention can also be used for separating one or more clearly defined polyglycerols, which do not "pass out" either at the head or the tail during the passage of the mixture on the particular phase, followed by elution. In this case, two passages are used. During the first elution, the fraction containing the constituent or constituents which it is wished to separate is retained, while a second passage makes it possible to separately collect said constituent or constituents.

Thus, for example, if it is wished to isolate polyglycerol of DP 5 (pentaglycerol), during a first passage it would be possible to subdivide the mixture into two fractions with a "cut" between tetraglycerol (DP=4) and pentaglycerol, retaining the fraction containing the pentaglycerol and polyglycerols of higher DP and then, during the elution of said fraction, the "cut" is made between the pentaglycerol and the hexaglycerol (DP=6).

It would also be possible to make the "cuts" in the reverse order, i.e. between the pentaglycerol and the hexaglycerol during the first passage on the column and while retaining the fraction containing the pentaglycerol and the polyglycerols with the lower DP (as well as the glycerol) and then during the elution of said fraction the "cut" would be made between the pentaglycerol and the tetraglycerol.

The process according to the invention makes it possible to separate the constituents with a purity generally between approximately 75 and 90%. Such purity levels generally satisfy industrial requirements, because they meet the prescribed contamination standards in various applications of polyglycerols. However, it is possible to improve the degree of purity of the separated constituents by acting on the process operating conditions. Thus, it would e.g. be possible to perform each "cut" so as to only retain in the sought fraction less than 5 wt. % of undesirable constituents.

EXAMPLES

Example 1

Example 1 illustrates the invention in the case of a continuous, simulated countercurrent process. The charge to be separated is constituted by a crude, synthetic industrial mixture containing cyclic structures, polyglycerols with degrees of polymerization (DP) varying between 2 and 10, glycerol residues and the corresponding isomers. The mean composition of the charge is as follows (wt. %):

| | |
|---|---|
| cyclic diglycerols | 5.7% |
| glycerol | 10.3% |
| diglycerol | 18.6% |
| triglycerol | 18.6% |
| tetraglycerol | 13.4% |
| pentaglycerol | 9.9% |
| hexaglycerol | 7.2% |
| heptaglycerol | 6.4% |
| octaglycerol | 4.3% |
| nonaglycerol | 3.6% |
| decaglycerol | 2.0% |
| | 100.0% |

The aim is to separate this mixture into two fractions, namely a fraction containing compounds ranging between cyclic diglycerols and tetraglycerol and a fraction including all the compounds from pentaglycerol to decaglycerols.

The system used consists of 24 glass columns with a mobile piston in order to compensate the volume variation due to the swelling of the resin, each having a length of 0.80 m (i.e. 19.2 m useful length) and an internal diameter of 15 mm. The columns are lined with an industrial divinyl benzene-styrene resin containing 4.5% DVB, having a mean particle diameter of 340 micrometers, a pseudoporosity of 50% with pores having a size close to $80 \times 10^{-8}$ cm. The resin is in acid form ($H^+$).

The general temperature of the system is maintained at 65° C. The eluent passed into these columns is constituted by an aqueous solution of sulphuric acid with a concentration of 0.005N and with a flow rate of 0.80 liter/hour.

The charge to be separated diluted in 50 wt. % pure water is introduced at a flow rate of 0.16 liter/hour. The average recycling rate is 2.0 liters/hour. As can be seen in FIG. 1, there is a sequential and synchronous translation of the injection points of the charge (CH) and the eluent (EL), as well as the drawing off points of the extract (EX) and the refined product (RA). The fluid is recycled by the pipe (RE) with the aid of the pump (P), as in a real countercurrent. The extract, which is the product most adsorbed by the resin, contains glycerol and products with a (DP) between 2 and 4 inclusive. The refined product, which is the least adsorbed product, contains products with a DP from 5 to 10.

Figure 2:
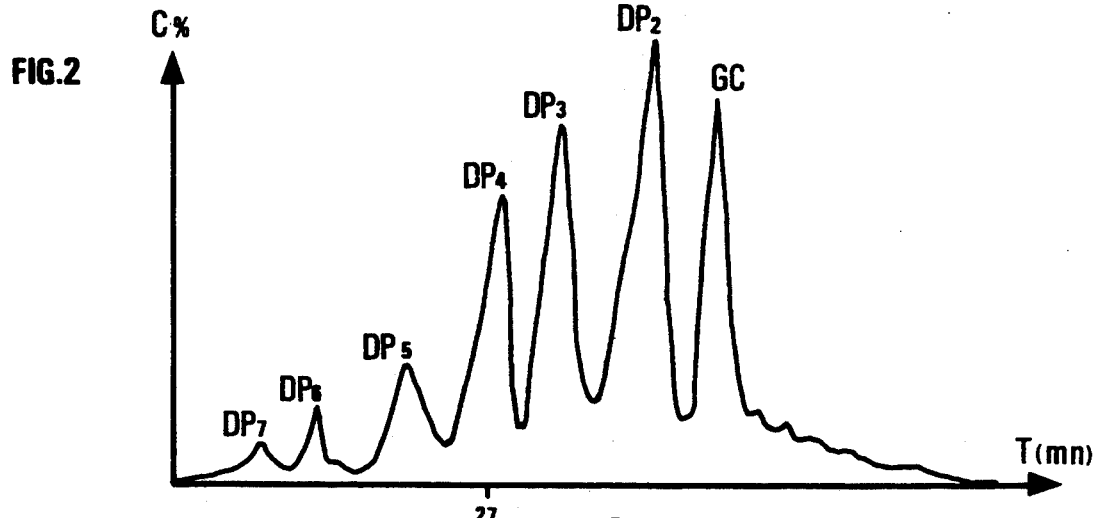
FIG. 2 shows an analytical chromatogram of a charge.
Figure 3:
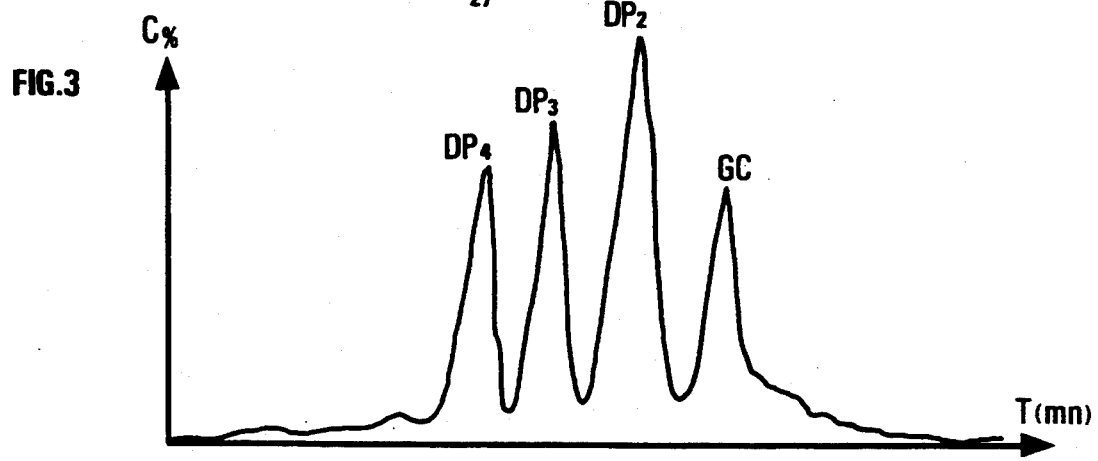
FIG. 3 shows a chromatogram of extract containing tetraglycerol.

FIG. 2 shows the analytical chromatogram of the charge and FIG. 3 the chromatogram of the extract containing the sought tetraglycerol, while the products with a higher DP are collected in the refined product. The weight percentage is plotted on the ordinate axis and the abscissa axis gives the time in minutes for the retention of the different compounds.

The extract has the following composition by weight:

| | |
|---|---|
| cyclic diglycerols | 2.56% |
| glycerol | 4.63% |
| diglycerol | 8.37% |
| triglycerol | 8.30% |
| tetraglycerol | 6.08% |
| DP above 4 | 0.06% |
| water | 70.00% |

The refined product has the following weight composition:

| | |
|---|---|
| pentaglycerol | 2.06% |
| hexaglycerol | 1.50% |
| heptaglycerol | 1.34% |
| octaglycerol and DP>8 | 2.07% |
| water | 93.03% |

Example 2

It is wished to obtain tetraglycerol in the pure state.

In example 1 the initial charge was separated into two fractions. The first fraction (extract 1) contains all the members with a degree of polymerization of 4 and below, while the second fraction (refined product 1) contains all the members with a degree of polymerization of 5 and above. To obtain the sought tetraglycerol, the extract 1 undergoes a further chromatographic separation in the same installation.

This extract has the following weight composition:

| | |
|---|---|
| cyclic diglycerols | 2.56% |
| glycerol | 4.63% |
| diglycerol | 8.37% |
| triglycerol | 8.30% |
| tetraglycerol | 6.08% |
| DP>4 | 0.06% |
| water | 70.0% |

The charge is passed under a flow rate of 0.18 liter/hour.

The eluent used consists of an aqueous solution of sulphuric acid with a concentration of 0,005N with a flow rate of 0.90 liter/hour. The average recycling flow rate is 2.01 liters/hour.

As can be seen in FIG. 1, there is a sequential and synchronous displacement of the injection points of the charge (CH) and the eluent (EL), as well as the drawing off points of the extract (EX) and the refined product (RA). The fluid is recycled by the pipe (RE) with the aid of the pump (P).

Figure 5:
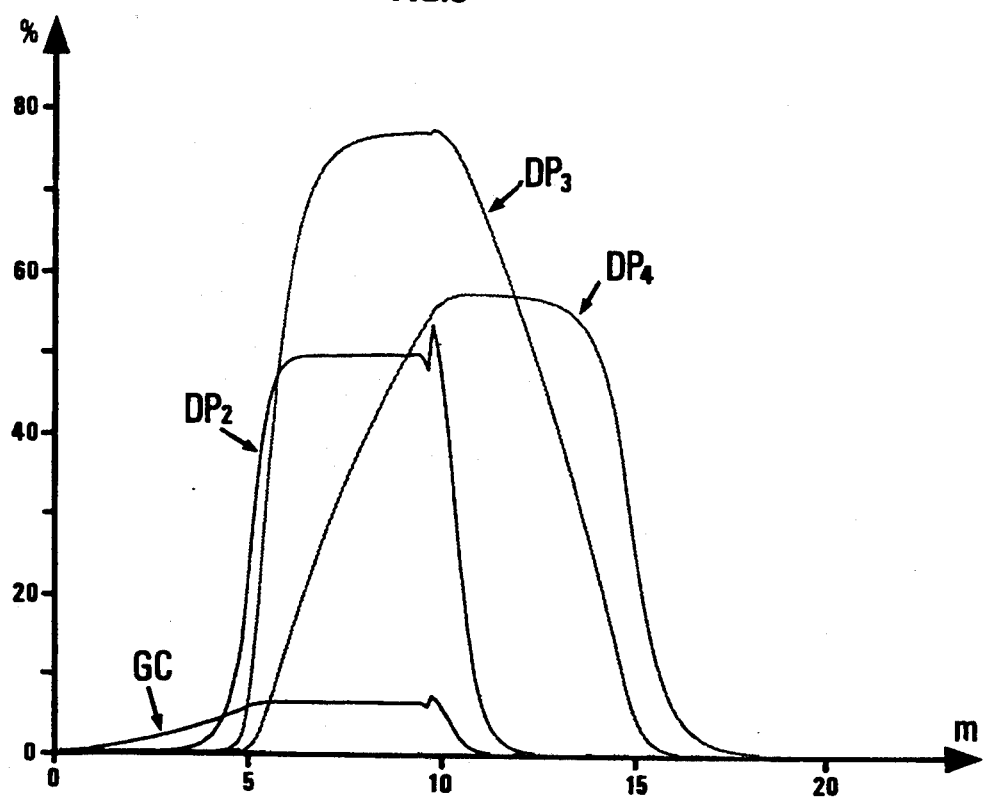
FIG. 5 shows a profile of concentration in the separation circuit.

FIG. 5 represents the profile of the concentrations in the separation circuit. On the ordinate is plotted the weight percentage of the concentrations of the compounds and on the abscissa the column length in meters. The curve GC corresponds to the variation in the concentrations of the sum of the glycerol and the cyclic compounds. The extract, which is the product most absorbed by the resin, contains glycerol and the products with a degree of polymerization 2 and 3, together with the cyclic diglycerol. It has the following composition by weight:

| | |
|---|---|
| DP cyclic + glycerol | 0.58% |
| DP2 | 2.99% |
| DP3 | 1.53% |
| water | 94.90% |

The refined product, which is the least adsorbed product, contains tetraglycerol. Its weight composition is as follows:

| | |
|---|---|
| DP<4 | 1.00% |
| tetraglycerol | 2.91% |
| DP>4 | 0.04% |
| water | 96.05% |

Figure 4:
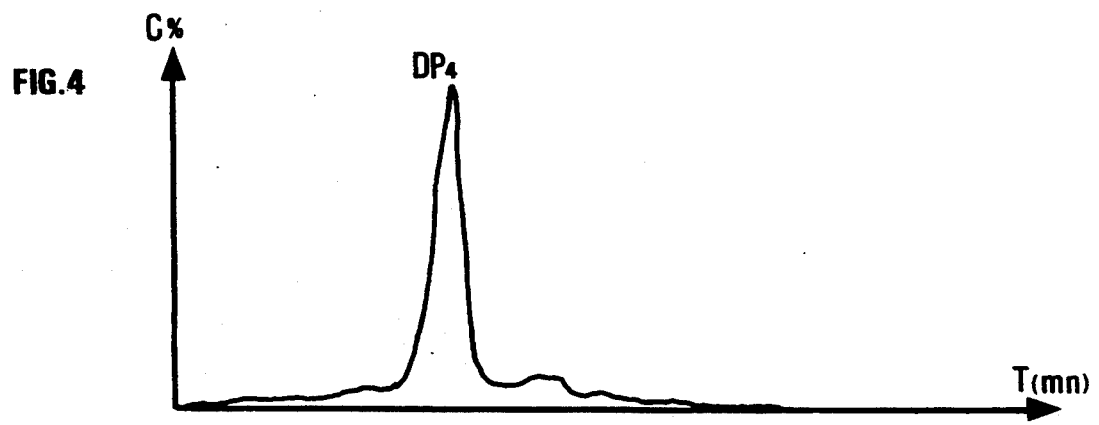
FIG. 4 shows tetraglycerol obtained following the elimination of constituents with a DP below 4.

FIG. 4 represents the tetraglycerol obtained alone following the elimination of the constituents with a DP below 4.

Example 3

Figure 6:
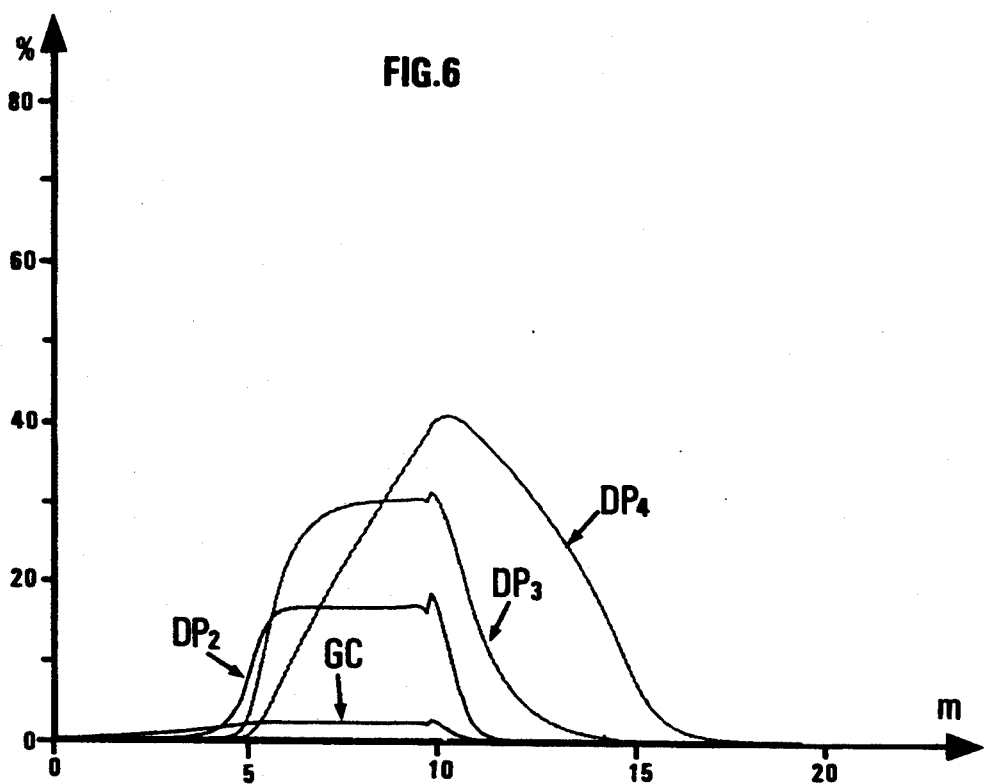
FIG. 6 shows a profile of concentrations when there are variations in the injection rates of the charge and the eluent and the flow rate of recycling in the system to increase DP4 purity.

It is possible to increase the purity of the sought DP4 by allowing variations in the injection rates of the charge and the eluent and the flow rate of recycling in the system. In this case the profile of the concentrations in the column is illustrated by FIG. 6.

The flow rates are then fixed to the following values:

| | |
|---|---|
| charge flow rate (extract 1) | 0.06 l/h |
| eluent flow rate | 0.78 l/h |
| recycling flow rate | 1.98 l/h |

Weight concentration of the constituents in the extract:

| | |
|---|---|
| cyclic diglycerols + glycerol | = 0.19% |
| DP2 | = 0.63% |
| DP4 | = 0.15% |
| H20 | = 99.03% |

Weight concentration of the constituents present in the refined product:

| | |
|---|---|
| cyclic diglycerols + glycerol | = 0% |
| DP2 | = 0% |
| DP3 | = 0.015% |
| DP4 | = 0.920% |
| H20 | = 99.065% |

We claim:

1. A process for the separation of at least one constituent of a mixture containing at least two polyglycerols having degrees of polymerization corresponding to integral values of 2 to 10, comprising passing said mixture into at least one column in contact with a particular phase through which flows a liquid eluent, wherein said particular phase is at least one organic cationic divinyl benzene-styrene copolymer resin wherein the cation is H+ and wherein the liquid eluent is an aqueous phase containing sulfuric acid with a normality of 0.001 to 0.01N.

2. A process according to claim 1, wherein the organic resin is a resin in the form of monocalibrated spherical grains had has a grain size below 500 micrometers.

3. A process according to claim 1, wherein the temperature of the system is below 80° C.

4. A process according to claim 1, wherein continuous operation takes place according to a real or simulated countercurrent system.

5. A process according to claim 1, wherein operation takes place according to a real or simulated cocurrent system.

6. A process according to claim 1, wherein a mixture of polyglycerols is separated in one pass into two fractions with two consecutive integral values of the degree of polymerization.

7. A process according to claim 1, wherein a mixture of polyglycerols is separated in two passes, to produce a polyglycerol having a given degree of polymerization value.

8. A process for the separation of at least one constituent of a mixture containing at least two polyglycerols having degrees of polymerization corresponding to integral values of 2 to 10, comprising passing said mixture into at least one column in contact with a particular phase through which flows a liquid eluent, wherein said particular phase is at least one organic cationic divinyl benzene-styrene copolymer resin wherein the cation is $H^+$ and wherein the liquid eluent is an aqueous phase to which is optionally added a strong acid.

* * * * *